(12) United States Patent
Wang et al.

(10) Patent No.: US 12,231,225 B2
(45) Date of Patent: Feb. 18, 2025

(54) REMOTE CONTROL SYSTEM AND REMOTE CONTROL METHOD FOR MAGNETIC CAPSULE ENDOSCOPE

(71) Applicant: Ankon Medical Technologies (Shanghai) Co., LTD., Shanghai (CN)

(72) Inventors: Tingqi Wang, Wuxi (CN); Xin Liu, Wuxi (CN); Xiaodong Duan, Pleasanton, CA (US); Pengsong Ji, Beijing (CN)

(73) Assignees: ANKON MEDICAL TECHNOLOGIES (SHANGHAI) CO., LTD., Wuhan (CN); ANX IIP HOLDING PTE. LTD., Singapore (SG)

( * ) Notice: Subject to any disclaimer, the term of this patent is extended or adjusted under 35 U.S.C. 154(b) by 23 days.

(21) Appl. No.: 16/988,691

(22) Filed: Aug. 9, 2020

(65) Prior Publication Data
US 2021/0059508 A1    Mar. 4, 2021

(30) Foreign Application Priority Data
Aug. 9, 2019    (CN) .......................... 201910738996.9

(51) Int. Cl.
*H04B 7/26* (2006.01)
*A61B 1/00* (2006.01)
(Continued)

(52) U.S. Cl.
CPC ........... *H04B 7/26* (2013.01); *A61B 1/00006* (2013.01); *A61B 1/00016* (2013.01);
(Continued)

(58) Field of Classification Search
CPC ............ A61B 1/00039; A61B 1/00016; A61B 1/00158; A61B 1/00006; H04B 7/26
See application file for complete search history.

(56) References Cited

U.S. PATENT DOCUMENTS 4,559,555 A * 12/1985 Schoolman .......... H04N 13/332
348/E13.008
5,876,325 A * 3/1999 Mizuno .................. A61B 34/37
600/117
(Continued)

FOREIGN PATENT DOCUMENTS

| CN | 203815419 U | 9/2014 |
|---|---|---|
| CN | 104244812 A | 12/2014 |

(Continued)

*Primary Examiner* — John P Leubecker
*Assistant Examiner* — Jae Woo (57) ABSTRACT

A remote control system and a remote control method for a magnetic capsule endoscope are provided. The remote control system includes a console and a computing terminal device. The console includes a base and one or more joysticks installed on the base, where the joysticks generate a first electrical signal according to a shaking operation. The computing terminal device converts the first electrical signal to a first control instruction and sends the first control instruction to an industrial personal computer of a controlled device through a telecommunication connection. The first control instruction instructs a drive mechanism of the controlled device to drive a magnetic moving component of the controlled device to perform a first motion. The magnetic moving component controls the movement of the magnetic capsule endoscope through a magnetic field of the controlled device when the first motion is performed.

16 Claims, 4 Drawing Sheets

(51) Int. Cl.
    *A61B 1/04* (2006.01)
    *H04R 1/02* (2006.01)
(52) U.S. Cl.
    CPC ...... *A61B 1/00042* (2022.02); *A61B 1/00158* (2013.01); *A61B 1/041* (2013.01); *H04R 1/02* (2013.01)

(56) References Cited

U.S. PATENT DOCUMENTS

| | | | | |
|---|---|---|---|---|
| 6,364,888 | B1* | 4/2002 | Niemeyer | A61B 34/37 348/E13.016 |
| 6,436,107 | B1* | 8/2002 | Wang | A61B 34/75 606/139 |
| 6,522,906 | B1* | 2/2003 | Salisbury, Jr. | A61B 34/30 600/407 |
| 6,850,817 | B1* | 2/2005 | Green | A61B 34/72 348/E13.016 |
| 8,406,750 | B2* | 3/2013 | Sonnenrein | H04W 76/10 455/445 |
| 2002/0087232 | A1* | 7/2002 | Lapham | B25J 9/161 700/245 |
| 2002/0120254 | A1* | 8/2002 | Julian | A61B 34/76 606/1 |
| 2005/0085696 | A1* | 4/2005 | Uchiyama | A61B 1/00147 600/128 |
| 2006/0178559 | A1* | 8/2006 | Kumar | G16H 40/63 600/109 |
| 2006/0253004 | A1* | 11/2006 | Frisch | G16H 30/20 600/300 |
| 2007/0059990 | A1* | 3/2007 | Kura | A61B 1/04 439/733.1 |
| 2007/0167715 | A1* | 7/2007 | Shigemori | A61B 1/00016 600/407 |
| 2008/0114224 | A1* | 5/2008 | Bandy | A61B 8/4236 600/459 |
| 2008/0300458 | A1* | 12/2008 | Kim | A61B 34/73 600/118 |
| 2010/0099948 | A1* | 4/2010 | Kimoto | A61B 1/00016 600/109 |
| 2011/0004059 | A1* | 1/2011 | Arneson | A61B 1/00045 600/109 |
| 2011/0245604 | A1* | 10/2011 | Yeh | A61B 1/041 600/109 |
| 2011/0275893 | A1* | 11/2011 | Kawano | A61B 1/00036 600/109 |
| 2012/0095289 | A1* | 4/2012 | Kawano | A61B 1/00158 600/109 |
| 2013/0041217 | A1* | 2/2013 | Kawano | A61B 1/041 600/109 |
| 2013/0267788 | A1* | 10/2013 | Duan | G06T 7/62 600/300 |
| 2014/0148643 | A1* | 5/2014 | Kawano | A61B 5/704 600/102 |
| 2015/0018615 | A1* | 1/2015 | Duan | A61B 1/00006 600/109 |
| 2015/0105797 | A1* | 4/2015 | Kim | A61B 1/00156 901/1 |
| 2016/0166133 | A1* | 6/2016 | Chiba | A61B 5/1116 600/109 |
| 2016/0210411 | A1* | 7/2016 | Mentis | G06F 3/04842 |
| 2017/0020375 | A1* | 1/2017 | Chiba | A61B 1/00158 |
| 2017/0035520 | A1* | 2/2017 | Duan | A61B 17/0218 |
| 2017/0042450 | A1* | 2/2017 | Tanaka | A61B 1/00 |
| 2017/0164816 | A1* | 6/2017 | Kawano | G06T 7/70 |
| 2018/0153383 | A1* | 6/2018 | Goshayesh | A61B 1/0005 |
| 2019/0365211 | A1* | 12/2019 | Duan | A61B 90/50 |
| 2020/0261180 | A1* | 8/2020 | Meglan | A61B 34/37 |

FOREIGN PATENT DOCUMENTS

| | | |
|---|---|---|
| CN | 205338891 U | 6/2016 |
| CN | 105852783 A | 8/2016 |
| CN | 107157512 A | 9/2017 |
| CN | 206880655 U | 1/2018 |
| CN | 107846462 A | 3/2018 |

\* cited by examiner

REMOTE CONTROL SYSTEM AND REMOTE CONTROL METHOD FOR MAGNETIC CAPSULE ENDOSCOPE

CROSS-REFERENCE OF RELATED APPLICATIONS

The application claims priority to Chinese Patent Application No. 201910738996.9 filed on Aug. 9, 2019, the contents of which are incorporated by reference herein.

FIELD OF INVENTION

The present invention relates to a medical device and more particularly to a remote control system and a remote control method for magnetic capsule endoscope.

BACKGROUND

Capsule endoscopy has been used more and more clinically because of its features such as no intubation, good comfort, and no cross-infection. The capsule endoscopy examines digestive tract in detail, and the capsule endoscopy is controlled via an external control device.

However, in the process of clinical application and promotion of the capsule endoscope and the external control device, it often encounters problems such as difficulty in operation training and slow mastering of operations, and skilled operation skills require more experience to achieve. Without professional operators, it is difficult to apply the capsule endoscope and the external control device, especially in the areas and emergency rooms short of doctors.

No effective solution has been found for the above problems.

SUMMARY OF THE INVENTION

The present invention provides a remote control system and a remote control method for magnetic capsule endoscope to at least solve the problem of inconvenient control of a capsule endoscope control device.

In an embodiment, a remote control system for magnetic capsule endoscope is provided. The remote control system comprises a console that comprises a console comprising a base and one or more joysticks installed on the base, wherein the one or more joysticks generate a first electrical signal according to a shaking operation; a computing terminal device converts the first electrical signal to a first control instruction and sends the first control instruction to an industrial personal computer of a controlled device through a telecommunication connection, wherein the first control instruction instructs a drive mechanism of the controlled device to drive a magnetic moving component of the controlled device to perform a first motion. The magnetic moving component controls the movement of the magnetic capsule endoscope through a magnetic field of the controlled device when the first motion is performed.

Further, the computing terminal device is installed with a remote operation client to convert the first electrical signal to the first control instruction and to send the first control instruction to the industrial personal computer. The industrial personal computer is installed with a server corresponding to the remote operation client, and the server converts the first control instruction to a drive signal for controlling the drive mechanism.

Further, the console comprises a touch panel disposed on the base for generating a second electrical signal according to a received touch operation. The computing terminal device further converts the second electrical signal to a second control instruction and sends the second control instruction to the controlled device via the telecommunication connection to control the magnetic moving component to perform a second motion.

Further, the console comprises a touch panel disposed on the base for generating a third electrical signal according to a received touch operation. The computing terminal device converts the third electrical signal to a third control instruction and sends the third control instruction to the magnetic capsule endoscope via the telecommunication connection to control the magnetic capsule endoscope to perform specified operations.

Further, the console comprises a button set on the top of a joystick for generating a fourth electrical signal according to a received press operation. The computing terminal device further converts the fourth electrical signal to a fourth control instruction and sends the fourth control instruction to the magnetic capsule endoscope via the telecommunication connection, and the fourth control instruction controls a first camera of the magnetic capsule endoscope to take images and transmits the images to the computing terminal device via the telecommunication connection.

Further, the computing terminal device is also connected to a second camera disposed towards the controlled device via the telecommunication connection, and sends the images captured by the second camera to a display terminal device for display.

Further, the remote control system also comprises: a first microphone and a first loudspeaker. The computing terminal device sends the sound signals received by the first microphone to a second loudspeaker of the controlled device via the telecommunication connection, and the first loudspeaker plays the sound signals obtained by a second microphone of the controlled device.

Further, the drive mechanism of the controlled device comprises a three-dimensional translation drive mechanism and a rotation drive mechanism to drive the magnetic moving component to perform three-dimensional translation and rotation respectively. The joysticks of the console comprise a first joystick for controlling of the three-dimensional translation drive mechanism and a second joystick for controlling of the rotation drive mechanism, and when a joystick is manipulated to a specified position, the joystick controls the corresponding drive mechanism to drive the magnetic moving component to move in the direction corresponding to the specified position.

Further, the console and the computing terminal device communicate in wired or wireless mode.

In another embodiment, a remote control method is provided. This method comprises: sending a remote control request to an industrial personal computer of a controlled device by manipulating a computing terminal device through a console, or receiving a remote control request sent by the industrial personal computer to the computing terminal device; establishing a telecommunication connection between the computing terminal device and the industrial personal computer after the remote control request is agreed; and selecting a current control terminal between the computing terminal device and the industrial personal computer according to a control terminal switch instruction, wherein the control terminal switch instruction is an instruction generated by the computing terminal device according to an operation received by the console, or the control terminal switch instruction is an instruction received by the computing terminal device and sent by the industrial personal computer, and the current control terminal is the control terminal to control the controlled device.

The present invention enables a remote control of the drive mechanism of the controlled device through the joysticks of the console, and the device mechanism drives the magnetic moving component of the controlled device to control the movement of the magnetic capsule endoscope through the movement of magnetic field. It solves the technical problem of inconvenient control of capsule endoscope. By converting the signals of the joysticks into control instructions that instruct the drive mechanism through the computing terminal device and sending the instructions to the industrial personal computer of the controlled device via the telecommunication connection, it realizes the technical effect of controlling the capsule endoscope by a remote control of the controlled device.

BRIEF DESCRIPTION OF THE DRAWINGS

The accompanying drawings here provide a further understanding of the present invention and are incorporated in and constitute a part of the present invention. The schematic embodiments of the present invention and their descriptions are used to explain the invention and do not constitute undue limitations on the present invention.

DETAILED DESCRIPTION

In order to enable those skilled in the art to better understand the application, the present invention can be described in detail below with reference to the accompanying drawings and preferred embodiments. However, the embodiments are not intended to limit the invention, and obviously, the described embodiments are only a part of the embodiments of the present invention, but not all of them. In the absence of conflict, the embodiments of the present invention and the features in the embodiments can be combined with each other. All other embodiments obtained by those having ordinary skill in the art without creative work based on the embodiments of the present invention are included in the scope of the present invention.

It should be noted that the terms, such as "first" and "second", as described in the specification and claims of the present invention and the accompanying drawings are used only to distinguish similar objects but do not necessarily describe a particular sequence or order. It should be understood that the terms used in this way are interchangeable where appropriate, so that the embodiments of the present invention described herein can be performed in a sequence other than those diagrammed or described herein. In addition, the terms such as "comprise", "include" and "have" and any of their variants are intended to cover non-exclusive inclusions. For example, for a process, method, system, product or device that comprises a series of steps or units, it is not necessarily limited to list all the steps or units, but other unlisted or inherent steps or units can also be included in such process, method, product or device.

Embodiment 1

Figure 1:
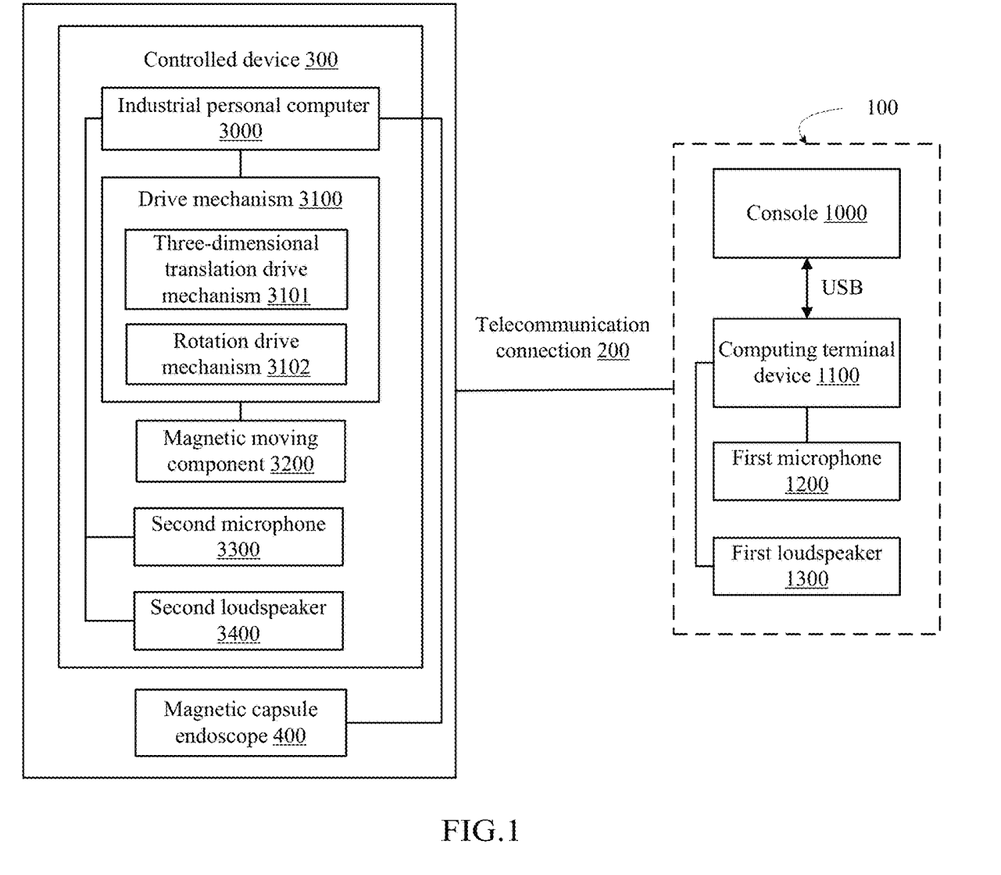
FIG. 1 shows a remote control system for magnetic capsule endoscope according to an embodiment of the present invention.

The embodiment provides a remote control system for magnetic capsule endoscope. The remote control system comprises a console and a computing terminal device, as shown in FIG. 1. The remote control system can be used to control a controlled device to move according to control operations on the remote control system, and the controlled device generates a moving magnetic field to control the motion of the magnetic capsule endoscope in a non-magnetic cavity (e.g. a human stomach).

The console comprises a base and one or more joysticks installed on the base, where the one or more joysticks are used to generate a first electrical signal according to a received shaking operation. The controlled device comprises an industrial personal computer (IPC), a drive mechanism, and a magnetic moving component. The computing terminal device is used to convert the first electrical signal to a first control instruction and send the first control instruction to the industrial personal computer of the controlled device through a telecommunication connection. The first control instruction is used to instruct the drive mechanism of the controlled device to drive the magnetic moving component of the controlled device to perform a first motion. The magnetic moving component is used to control the movement of the magnetic capsule endoscope by the movement of the magnetic field when the first motion is performed.

The console and the computing terminal device can communicate through a wired communication interface, such as USB serial interface, and can also communicate through wireless communication. The computing terminal device communicates with the IPC via a telecommunication connection. The physical layer of the telecommunication connection can include fiber optic communication, cable communication, and 3G, 4G and 5G wireless communications.

Figure 2:
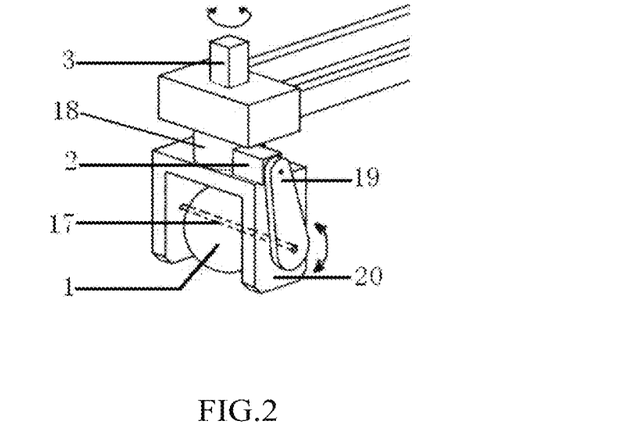
FIG. 2 shows a rotation drive mechanism and a magnetic moving component according to an embodiment of the present invention.

The drive mechanism of the controlled device comprises a three-dimensional translation drive mechanism and a rotation drive mechanism used to drive the magnetic moving component to perform three-dimensional translation and rotation respectively. FIG. 2 shows a rotation drive mechanism and a magnetic moving component of the controlled device. The magnetic moving component comprises a magnetic ball 1 for generating the magnetic field, the magnetic ball 1 is disposed in a frame 20. The rotation drive mechanism comprises a vertical motor 3 for driving the frame 20 to rotate around a vertical axis 18, and a horizontal motor 2 for driving a timing belt pulley 19 to make the magnetic ball 1 rotate around a horizontal axis 17. In addition, the drive mechanism further comprises the three-dimensional translation drive mechanism not shown in FIG. 2 for the translation motion of the device shown in FIG. 2 in all directions along the three-dimensional axis driven by a connecting arm.

Figure 3:
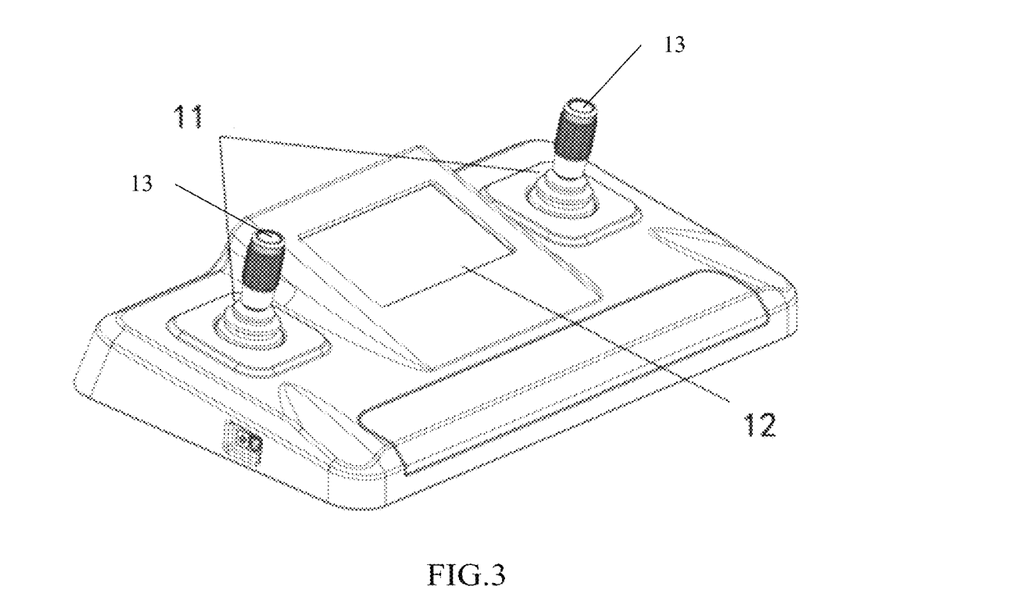
FIG. 3 shows a console of the remote control system for magnetic capsule endoscope according to an embodiment of the present invention.

As shown in FIG. 3, the console comprises two joysticks (11): a first joystick for controlling the three-dimensional translation drive mechanism and a second joystick for controlling the rotation drive mechanism.

As shown in FIG. 3, the console also comprises a touch panel 12 disposed on the base. The touch panel 12 can be a panel with physical buttons (13) or a touch screen that displays one or more function buttons.

The touch panel 12 can generate a second electrical signal according to the received touch operation. The computing terminal device converts the second electrical signal to a second control instruction and sends the second control instruction to the controlled device via the telecommunication connection to control the magnetic moving component to perform a second motion. The second motion is a preset motion process. For example, when the button represents the function of Allow Patient Access, it controls the magnetic moving component to move away to give patient space to get on and off the bed. When the button represents the function of Rotate the Capsule Vertically 45 Degrees, it controls the magnetic moving component to move to the position to rotate the capsule vertically 45 degrees.

The touch panel 12 can also generate a third electrical signal according to the received touch operation. The computing terminal device converts the third electrical signal to a third control instruction and sends the third control instruction to the magnetic capsule endoscope via the telecommunication connection to control the magnetic capsule endoscope to perform specified operations. The specified operations can include turning on and turning off the capsule endoscope, or controlling the capsule endoscope to take images.

In an alternative embodiment, the console also comprises a button disposed on the top of a joystick for generating a fourth electrical signal according to the received press operation. The computing terminal device converts the fourth electrical signal to a fourth control instruction and sends the fourth control instruction to the magnetic capsule endoscope via the telecommunication connection. The fourth control instruction is used to control a first camera of the magnetic capsule endoscope to take images and to transmit the images to the computing terminal device via the telecommunication connection.

The computing terminal device is also connected to a second camera disposed towards the controlled device via the telecommunication connection, and sends the images captured by the second camera to a display terminal device for display. The display terminal device can be a display screen of the computing terminal device, or a display screen of the IPC. The second camera of the controlled device is used to monitor the operating status of the controlled device. The camera can be arranged in different positions around the controlled device as needed to give the operator a better understanding of the operation status of the controlled device. The second camera can be placed at the sides, head or tail of the examination bed on which a subject is lying and at the same level as the subject to better observe the relative position of the magnetic moving component with the subject and thus to ensure the safety of the examination process. The second camera is placed as needed so its number can be one, two, three or four, etc.

Further, the remote control system comprises a first microphone and a first loudspeaker. The computing terminal device sends the sound signals received by the first microphone to a second loudspeaker of the controlled device via the telecommunication connection, and the first loudspeaker plays the sound signals obtained by a second microphone of the controlled device. Therefore, the operator of the remote control system can talk to those near the controlled device.

In the embodiment, a remote operation client (hereinafter referred to as client) is installed on the computing terminal device. The client is used to convert the electrical signals received from the console into corresponding control instructions, and send the control instructions to the IPC of the controlled device. The computing terminal device communicates with the IPC via telecommunication connection or via local area network or wide area network. The IPC is installed with a server corresponding to the remote operation client, and the server is used to convert control instructions to drive signals for controlling the drive mechanism. The server can be used to receive instructions from the client, and the client can also be used to receive the images taken by the capsule endoscope and the operating status of the controlled device transmitted from the server. Voice calls can also be made between the server and the client.

The remote control system provided in the embodiment is installed with a software, and the software assists the client to realize its functions. The client comprises functions such as device control, capsule control, information display, remote monitoring and voice interaction, etc.

The device control function controls the motion of the controlled device at distance through the joysticks or the touch panel on the console, and realizes the same effects as the control through the local IPC of the controlled device, including the three-dimensional translation motion and rotation motion.

The capsule control function controls the capsule endoscope in the same way as the controlled device does, such as controlling the capsule to take images, turning off the capsule or other capsule-related instructions.

The information display function displays the images taken by capsule endoscope, device status and other status information on the server in real time, and sends the relevant information to the client for display through the telecommunication connection. The motion status of the controlled device, including the real-time position and limit state of its three-dimensional translation, the angle of rotation, and the posture of the capsule endoscope, can be displayed in the local and remote interfaces in real-time animation to facilitate the capsule endoscope procedure.

The remote monitoring function monitors the operation of the controlled device in real time remotely through a main control terminal that can be either the client or the server and displays the images obtained by the server on the main control terminal in real time.

The voice interaction function can realize two-way real-time voice conversation and enable real-time communication between the client and the server.

In addition, an emergency stop instruction can be set up to stop the controlled device to ensure the safety of the remote operation. The network transmission of this instruction has the highest priority. The controlled device can be stopped after the instruction is issued by the console or the IPC.

Because the computing terminal device and the console communicate in wired or wireless mode, and the computing terminal device converts instructions by a client installed, the console can be connected to any computing terminal device installed with the client to control the controlled device remotely.

Based on a capsule endoscope control device (the controlled device described in the embodiment) and combined with computer technology, network communication technology and medical technology, the images taken by the capsule endoscope and the control data of the controlled device can be transmitted at high speed, and thus realizes the real-time remote control of the capsule endoscope.

In the embodiment, the capsule endoscope control device can be manipulated via remote control, which greatly eases the capsule endoscope examination. Therefore, it facilitates the clinical application and promotion of the capsule endoscope control device, and optimizes the allocation of medical resources, so that hospitals or other medical institutions without skilled endoscopy physicians can also offer real-time gastrointestinal examination by the capsule endoscope, which contributes to the digestive tract health of the general public.

Embodiment 2

This embodiment provides a remote control method executed by the remote control system of magnetic capsule endoscope provided in embodiment 1 and can be applied to the client. The client can run on a mobile terminal, a hand-held terminal or other similar computing devices. Running on different computing devices only means a difference in execution body. The person skilled in the art can foresee that the same technical effect can be produced though running on different operation devices.

Figure 4:
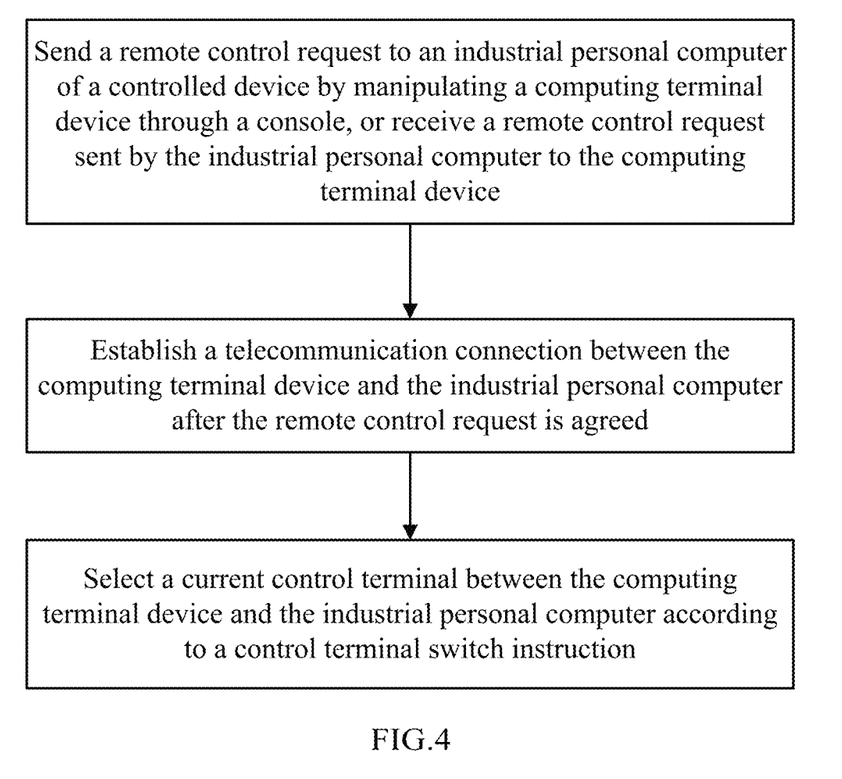
FIG. 4 shows a flowchart of a remote control method according to an embodiment of the present invention.

The remote control method provided in this embodiment, as shown in FIG. 4, comprises the following steps:

Step 101: Sending a remote control request to the IPC of the controlled device by manipulating the computing terminal device through the console, or receiving a remote control request sent by the IPC to the computing terminal device;

Step 102: Establishing a telecommunication connection between the computing terminal device and the IPC after the remote control request is agreed;

Step 103: Selecting the current control terminal between the computing terminal device and the IPC according to a control terminal switch instruction, wherein the control terminal switch instruction is an instruction generated by the computing terminal device according to an operation received by the console, or it is an instruction received by the computing terminal device and sent by the IPC, and the current control terminal is the control terminal allowed to control the controlled device.

The control terminal switch instruction is used to switch the main control terminal between the IPC of the controlled device and the remote control system of the magnetic capsule endoscope. In remote training, it is convenient to switch the current control terminal between the local controller (the controlled device) and the remote control system, so as to facilitate the training and teaching.

Figure 5:
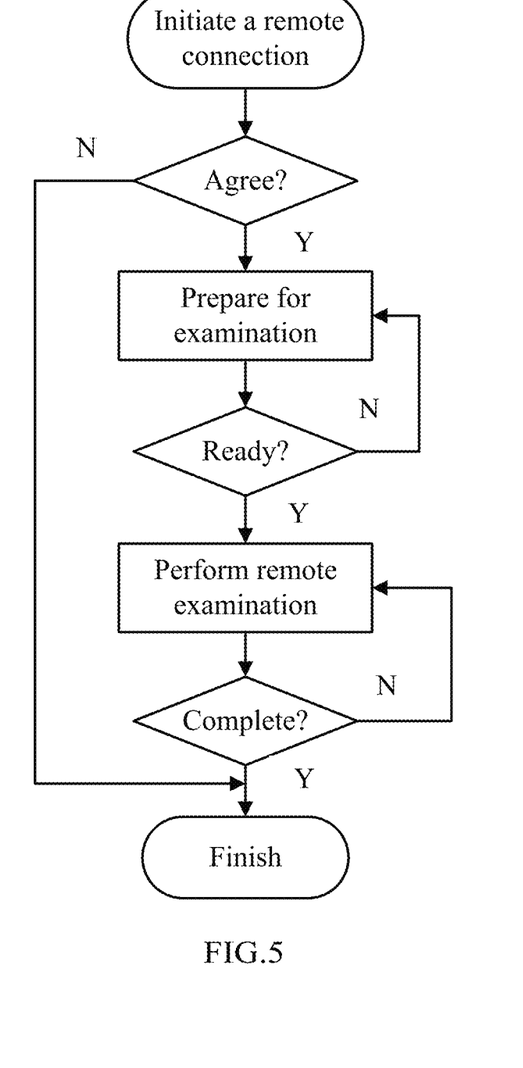
FIG. 5 shows a flowchart of another remote control method according to an embodiment of the present invention.

Referring to FIG. 5, the embodiment of the method is used in a specific application scenario, where the process of using the remote control system of the magnetic capsule endoscope comprises four steps: initiating a remote connection, preparing for examination, performing remote examination, and finishing examination.

In the case of a well-configured network on the server and the client, both the server and the client can initiate a remote control request and then test the connection after the other side agrees the request.

The step of preparing for examination mainly comprises checking whether the network delay at both sides meets the requirements of remote control and whether the remote control, the capsule endoscope images and other sensor information, the monitoring image and the voice interaction function are normal. It also comprises the preparation of the operator on the controlled device side, such as instructing the subject to do preparations and wear the recorder, entering information of the subject and helping the subject swallow the capsule endoscope, etc.

The step of performing remote examination is to manipulate the drive mechanism of the controlled device via the joysticks or the touch panel on the console. The operator can make adjustment in real time based on the received images taken by the capsule endoscope, other sensor information and the monitoring images of the cameras installed around the controlled device. They can also communicate with the operator or the subject on the controlled device side via voice calls.

The examination can be finished after confirming the examination process is completed.

It should be noted that the steps shown in the drawing can be performed on a computer system with a set of instructions that can be executed in a computer. Furthermore, although the logical sequence is shown in the flow chart, in some cases the steps shown or described here can be performed in a different sequence.

Elements included herein and list of the reference numbers are provided below.

1 magnetic ball
2 horizontal motor
3 vertical motor
17 horizontal axis
18 vertical axis
19 timing belt pulley
20 frame
11 joystick
12 touch panel
13 Button
100 Remote control system
300 Controlled device
3000 Industrial personal computer
3100 Drive mechanism
3101 Three-dimensional translation drive mechanism
3102 Rotation drive mechanism
3200 Magnetic moving component
3300 Second microphone
3400 Second loudspeaker
400 Magnetic capsule endoscope
200 Telecommunication connection
1000 Console
1100 Computing terminal device
1200 First microphone
1300 First loudspeaker Through the above description of the embodiment, the person skilled in the art can clearly understand that the method in above embodiment can be implemented based on software and necessary general-purpose hardware platform, or only based on hardware, but in many cases the former is a better way. Based on this understanding, the technical solution of the present invention is essentially is implemented or the part that contributes to prior art is implemented in the form of a software product. The software product is stored in a storage medium (such as ROM/RAM, diskette, CD), and comprises a plurality of instructions to instruct a terminal device (a mobile phone, computer, server, or network equipment, etc.) to execute the method described in each embodiment of the present invention.

The person skilled in the art realizes that the present invention by no means is limited to the preferred embodiments described above. On the contrary, many modifications and variations are possible within the scope of the appended claims. Any modifications, equivalent substitutions, improvements, etc. made within the principles of the present invention are intended to be included within the scope of the present invention.

What is claimed is:
1. A remote control system for magnetic capsule endoscope, comprising:
a remote control console comprising a base and one or more joysticks installed on the base, wherein the one or more joysticks generate a first electrical signal according to a shaking operation;

a computing terminal device and, a local controlled device, comprising a local industrial personal computer, a local drive mechanism and a magnetic moving component;

wherein the remote control console and the computing terminal device are disposed at a distant location, off site from the local controlled device, the computing terminal device installed with a remote operation client converts the first electrical signal to a first control instruction and sends the first control instruction to the local industrial personal computer of the local controlled device through a telecommunication connection, wherein the local industrial personal computer is installed with a server corresponding to the remote operation client, and the server converts the first control instruction to a drive signal for controlling the local drive mechanism, wherein the first control instruction instructs the local drive mechanism of the local controlled device to drive the magnetic moving component of the local controlled device to perform a first motion, and the magnetic moving component controls the movement of the magnetic capsule endoscope through a magnetic field of the local controlled device when the first motion is performed;

wherein the computing terminal device is configured to, after the remote control request is agreed, switch on the local industrial personal computer or the remote control console to be a current main control terminal, based on whether, respectively the local industrial personal computer sends a control terminal switch instruction or the remote control console sends the control terminal switch instruction to the computing terminal device, when the remote control console serves as the current main control terminal, the computing terminal device converts the first electrical signal generated by the remote control console to a first control instruction and sends the first control instruction to the local industrial personal computer of the local controlled device, the local industrial personal computer drives the magnetic moving component to move based on the first control instructions instructed by the remote control console, and when the local industrial personal computer acts as the current main control terminal, the local industrial personal computer, independent from the computing terminal device, directly generates control signals to instruct the local drive mechanism to move the magnetic moving component.

2. The remote control system of claim 1, wherein the remote control console further comprises a touch panel disposed on the base for generating a second electrical signal according to a received touch operation; and wherein the computing terminal device further converts the second electrical signal to a second control instruction and sends the second control instruction to the local controlled device via the telecommunication connection to control the magnetic moving component to perform a second motion.

3. The remote control system of claim 1, wherein the remote control console further comprises a touch panel disposed on the base for generating a third electrical signal according to a received touch operation; and wherein the computing terminal device converts the third electrical signal to a third control instruction and sends the third control instruction to the magnetic capsule endoscope via the telecommunication connection to control the magnetic capsule endoscope to perform specified operations.

4. The remote control system of claim 1, wherein the remote control console further comprises a button set on the top of a joystick for generating a fourth electrical signal according to a received press operation; and wherein the computing terminal device further converts the fourth electrical signal to a fourth control instruction and sends the fourth control instruction to the magnetic capsule endoscope via the telecommunication connection, and the fourth control instruction controls a first camera of the magnetic capsule endoscope to take images and transmits the images to the computing terminal device via the telecommunication connection.

5. The remote control system of claim 1, further comprising a second camera disposed such that the local controlled device is in the field of view, the second camera configured to monitor an operating status of the local controlled device;

wherein the computing terminal device is also connected to a second camera via the telecommunication connection, and sends the images captured by the second camera to a display terminal device for display.

6. The remote control system of claim 1, further comprising: a first microphone; a first loudspeaker; wherein the computing terminal device sends the sound signals received by the first microphone to a second loudspeaker of the local controlled device via the telecommunication connection, and the first loudspeaker plays the sound signals obtained by a second microphone of the local controlled device.

7. The remote control system of claim 1, wherein the drive mechanism of the local controlled device comprises a three-dimensional translation drive mechanism and a rotation drive mechanism to drive the magnetic moving component to perform three-dimensional translation and rotation respectively; and wherein the joysticks of the remote control console comprise a first joystick for controlling of the three-dimensional translation drive mechanism and a second joystick for controlling of the rotation drive mechanism, and when a joystick is manipulated to a specified position, the joystick controls the corresponding drive mechanism to drive the magnetic moving component to move in the direction corresponding to the specified position.

8. The remote control system of claim 1, wherein the remote control console and the computing terminal device communicate in wired or wireless mode;

wherein the computing terminal device converts instructions by a client installed, and the remote control console is able to be connected to any computing terminal device installed with the client.

9. The remote control system of claim 1, wherein a main control terminal is the client or the server, and the main control terminal monitors an operation of the local controlled device in real time remotely, and displays the images obtained by the server on the main control terminal in real time.

10. The remote control system of claim 1, wherein either the remote control console or the local industrial personal computer is able to issue an emergency stop instruction to control the local controlled device to stop, and a network transmission of the emergency stop instruction has the highest priority.

11. The remote control system of claim 1, further comprising a second camera disposed such that the controlled device is in the field of view and/or arranged around the controlled device, the second camera configured to monitor an operating status of the controlled device;

wherein the remote computing terminal device is also connected to a second camera via the telecommunication connection, and sends the images captured by the second camera to a display terminal device for display.

12. A remote control method for magnetic capsule endoscope, comprising: sending a remote control request to a local industrial personal computer by manipulating a remote computing terminal device through a remote control console, or receiving the remote control request sent by the local industrial personal computer to the remote computing terminal device;
- establishing a telecommunication connection between the remote computing terminal device and the local industrial personal computer after the remote control request is agreed;
- switching a current main control terminal between the remote control console and the industrial personal computer of the local controlled device according to a control terminal switch instruction, wherein the control terminal switch instruction is an instruction sent by one of the remote control console and the industrial personal computer to the remote computing terminal device and a main control terminal is selected as a current control terminal to control the local controlled device,
- when the remote control console at the remote place serves as the current main control terminal, the remote computing terminal device converts the first electrical signal generated by the remote control console at a distant location, offsite from the local controlled device, to a first control instruction and sends the first control instruction to the local industrial personal computer of the local controlled device, the local industrial personal computer drives the magnetic moving component to move based on the first control instructions instructed by the remote control console, and when the local industrial personal computer acts as the current main control terminal, the local industrial personal computer, independent from the remote computing terminal device, directly generates control signals to instruct the local drive mechanism on site to move the magnetic moving component.

13. A remote control system for magnetic capsule endoscope, comprising:
- a remote control console comprising a base and one or more joysticks installed on the base;
- a remote computing terminal device communicating with the remote control console to receive signals from the joystick of the remote control console;
- a local controlled device, comprising an industrial personal computer, a local drive mechanism and a magnetic moving component;
- wherein the remote control console and the remote computing terminal device are disposed off site, distant from the local controlled device, wherein the remote computing terminal device is installed with a remote operation client, and the industrial personal computer is installed with a server corresponding to the remote operation client, wherein the remote computing terminal device communicates with the industrial personal computer of the controlled device through a telecommunication mechanism, which comprises fiber optic communication, cable communication, or 3G, 4G or 5G wireless communications, wherein the industrial personal computer instructs the drive mechanism to drive a magnetic moving component of the controlled device to perform a first motion based on signals sent by the joystick, wherein the magnetic moving component controls a movement of a magnetic capsule endoscope through a magnetic field of the controlled device when the first motion is performed;
- wherein the remote computing terminal device is configured to switch either the local industrial personal computer or the remote control console to be a current control terminal based on that the industrial personal sends a control terminal switch instruction or the remote control console sends the control terminal switch instruction to the remote computing terminal device,
- when the remote control console serves as the current main control terminal, the remote computing terminal device converts the first electrical signal generated by the remote control console to a first control instruction and sends the first control instruction to the industrial personal computer of the controlled device, the local industrial personal computer on site drives the magnetic moving component to move based on the first control instructions instructed by the remote control console, and when the local industrial personal computer acts as the current main control terminal, the local industrial personal computer, independent from the remote computing terminal device, directly generates control signals to instruct the local drive mechanism to move said magnetic moving component.

14. The remote control system of claim 13, further comprising:
- a first microphone;
- a first loudspeaker; wherein the remote computing terminal device sends the sound signals received by the first microphone to a second loudspeaker of the controlled device via the telecommunication connection, and the first loudspeaker plays the sound signals obtained by a second microphone of the controlled device.

15. The remote control system of claim 13, wherein the remote computing terminal device is further configured to communicate with the magnetic capsule endoscope through the telecommunication mechanism, and the remote control console further comprises a button set on a top of the joystick for controlling a camera of the magnetic capsule endoscope to take images.

16. The remote control system of claim 13, wherein a drive mechanism of the local controlled device comprises a three-dimensional translation drive mechanism and a rotation drive mechanism to drive the magnetic moving component to perform three-dimensional translation and rotation respectively; and
- wherein the joysticks comprise a first joystick for controlling of the three-dimensional translation drive mechanism and a second joystick for controlling of the rotation drive mechanism.

\* \* \* \* \*